(12) United States Patent
Morioka et al.

(10) Patent No.: US 9,981,201 B2
(45) Date of Patent: May 29, 2018

(54) VERTICAL CENTRIFUGAL THIN FILM EVAPORATOR AND MONOMER PURIFICATION METHOD

(71) Applicant: Mitsubishi Chemical Corporation, Tokyo (JP)

(72) Inventors: Junichi Morioka, Otake (JP); Shuhei Otsuka, Otake (JP)

(73) Assignee: Mitsubishi Chemical Corporation, Tokyo (JP)

( * ) Notice: Subject to any disclaimer, the term of this patent is extended or adjusted under 35 U.S.C. 154(b) by 121 days.

(21) Appl. No.: 14/381,020

(22) PCT Filed: Feb. 5, 2013

(86) PCT No.: PCT/JP2013/052558
§ 371 (c)(1),
(2) Date: Aug. 26, 2014

(87) PCT Pub. No.: WO2013/136874
PCT Pub. Date: Sep. 19, 2013

(65) Prior Publication Data
US 2015/0038736 A1 Feb. 5, 2015

(30) Foreign Application Priority Data
Mar. 16, 2012 (JP) .................................. 2012-060209

(51) Int. Cl.
*B01D 1/22* (2006.01)
*C07C 67/58* (2006.01)

(52) U.S. Cl.
CPC .............. *B01D 1/225* (2013.01); *C07C 67/58* (2013.01)

(58) Field of Classification Search
CPC ................................ B01D 1/225; C07C 67/58
See application file for complete search history.

(56) References Cited

U.S. PATENT DOCUMENTS 3,020,211 A * 2/1962 Smith .................... B01D 1/225
159/49
3,067,812 A * 12/1962 Latinen .................. B01D 1/225
159/13.2
(Continued)

FOREIGN PATENT DOCUMENTS

CN 102139165 A 8/2011
JP 42-26175 12/1967
(Continued)

OTHER PUBLICATIONS

International Search Report dated May 7, 2013, in PCT/JP13/052558 filed Feb. 5, 2013.
(Continued)

*Primary Examiner* — Pancham Bakshi
*Assistant Examiner* — Mark R Luderer
(74) *Attorney, Agent, or Firm* — Oblon, McClelland, Maier & Neustadt, L.L.P.

(57) ABSTRACT

A vertical centrifugal thin film evaporator is equipped with: a cylindrical body in which an central axis of a circle is set in a vertical direction; a rotor that rotates an interior of the cylindrical body in a circumferential direction thereof; a wiper that slides on an inner circumferential surface of the cylindrical body; a fixing support that fixes the wiper and is mounted on the rotor; and a heater that heats a circumferential surface of the cylindrical body. A liquid-withdrawing structure that communicates between a space surrounded by the wiper and the fixing support and a space outside the wiper and the fixing support is formed on at least one of the wiper and the fixing support, thereby preventing a liquid to be processed from being retained between the wiper and the fixing support.

12 Claims, 4 Drawing Sheets

(56) References Cited

U.S. PATENT DOCUMENTS

| | | | |
|---|---|---|---|
| 3,130,108 A | 4/1964 | Eckstrom et al. | |
| 4,504,361 A * | 3/1985 | Tkac | B01D 1/222 |
| | | | 159/13.1 |
| 2004/0204608 A1 | 10/2004 | Yada et al. | |

FOREIGN PATENT DOCUMENTS

| | | |
|---|---|---|
| JP | 2003-170001 | 6/2003 |
| JP | 2011-33241 A | 2/2011 |

OTHER PUBLICATIONS

Combined Chinese Office Action and Search Report dated Apr. 1, 2015 in Patent Application No. 201380014339.0 (with English translation of categories of cited documents).

* cited by examiner

VERTICAL CENTRIFUGAL THIN FILM EVAPORATOR AND MONOMER PURIFICATION METHOD

TECHNICAL FIELD

The present invention relates to a vertical centrifugal thin film evaporator.

This application claims priority to Japanese Patent Application No. 2012-060209 filed on Mar. 16, 2012, the entire contents of which are incorporated by reference herein.

BACKGROUND ART

When materials that are easily polymerized and solidified by heat, materials that are degraded by heat, or materials having high viscosity are purified, a vertical centrifugal thin film evaporator may be used (for example, Patent Document 1).

As the vertical centrifugal thin film evaporator, for instance, one equipped with a cylindrical body in which an central axis of a circle is set in a vertical direction, a rotor that rotates the interior of the cylindrical body, a wiper that slides on an inner circumferential surface of the cylindrical body, a fixing support that fixes the wiper to the rotor, and a heater that heats the circumferential surface of the cylindrical body is widely used (Patent Document 1). The vertical centrifugal thin film evaporator purifies a material to be purified by introducing a liquid to be processed, which contains the material to be purified, into the interior of the cylindrical body, and by repetitively evaporating and condensing the material to be purified in the interior of the cylindrical body.

However, in the vertical centrifugal thin film evaporator described in Patent Document 1, the liquid to be processed was apt to be retained between the wiper and the fixing support. In the case of the liquid to be processed which was apt to be degraded by heat, if a retention time was prolonged, the liquid to be processed incurred thermal degradation to produce impurities or to give rise to contamination in the cylindrical body, thereby exerting an adverse influence on purification treatment or purity of the material to be purified. Further, in the case of the liquid to be processed which was apt to be polymerized by heat, if a retention time was prolonged, the liquid to be processed was polymerized and solidified, thereby impeding smooth operation of the vertical centrifugal thin film evaporator in some cases.

CITATION LIST

Patent Document

Patent Document 1: JP S42-26175 B

DISCLOSURE OF THE INVENTION

Problem to be Solved by the Invention

An object of the present invention is to provide a vertical centrifugal thin film evaporator and a monomer purification method, which prevents the retention of a liquid to be processed between a wiper and a fixing support.

Means for Solving Problem

The present invention has the following aspects.

[1] A vertical centrifugal thin film evaporator that includes: a cylindrical body in which an central axis of a circle is set in a vertical direction; a rotor configured to rotate an interior of the cylindrical body in a circumferential direction thereof; a wiper configured to slide on an inner circumferential surface of the cylindrical body; a fixing support configured to fix the wiper and mounted on the rotor; and a heater configured to heat a circumferential surface of the cylindrical body, wherein at least one of the wiper and the fixing support has a liquid-withdrawing structure that communicates between a space surrounded by the wiper and the fixing support and a space outside the wiper and the fixing support.

[2] In the vertical centrifugal thin film evaporator described in [1], the wiper may have a through-hole formed as the liquid-withdrawing structure.

[3] In the vertical centrifugal thin film evaporator described in [1] or [2], the wiper may have a notch formed as the liquid-withdrawing structure.

[4] In the vertical centrifugal thin film evaporator described in any one of [1] to [3], the fixing support may have a through-hole formed as the liquid-withdrawing structure.

[5] A monomer purification method of purifying a liquid containing a monomer having a vinyl group using the vertical centrifugal thin film evaporator described in [1].

Effect of the Invention

According to the vertical centrifugal thin film evaporator and the monomer purification method of the present invention, it is possible to prevent a liquid to be processed from being retained between a wiper and a fixing support. As a result, it is possible to stably operate the vertical centrifugal thin film evaporator.

MODE(S) FOR CARRYING OUT THE INVENTION

<Vertical Centrifugal Thin Film Evaporator>

An embodiment of the vertical centrifugal thin film evaporator of the present invention will be described.

Figure 1:
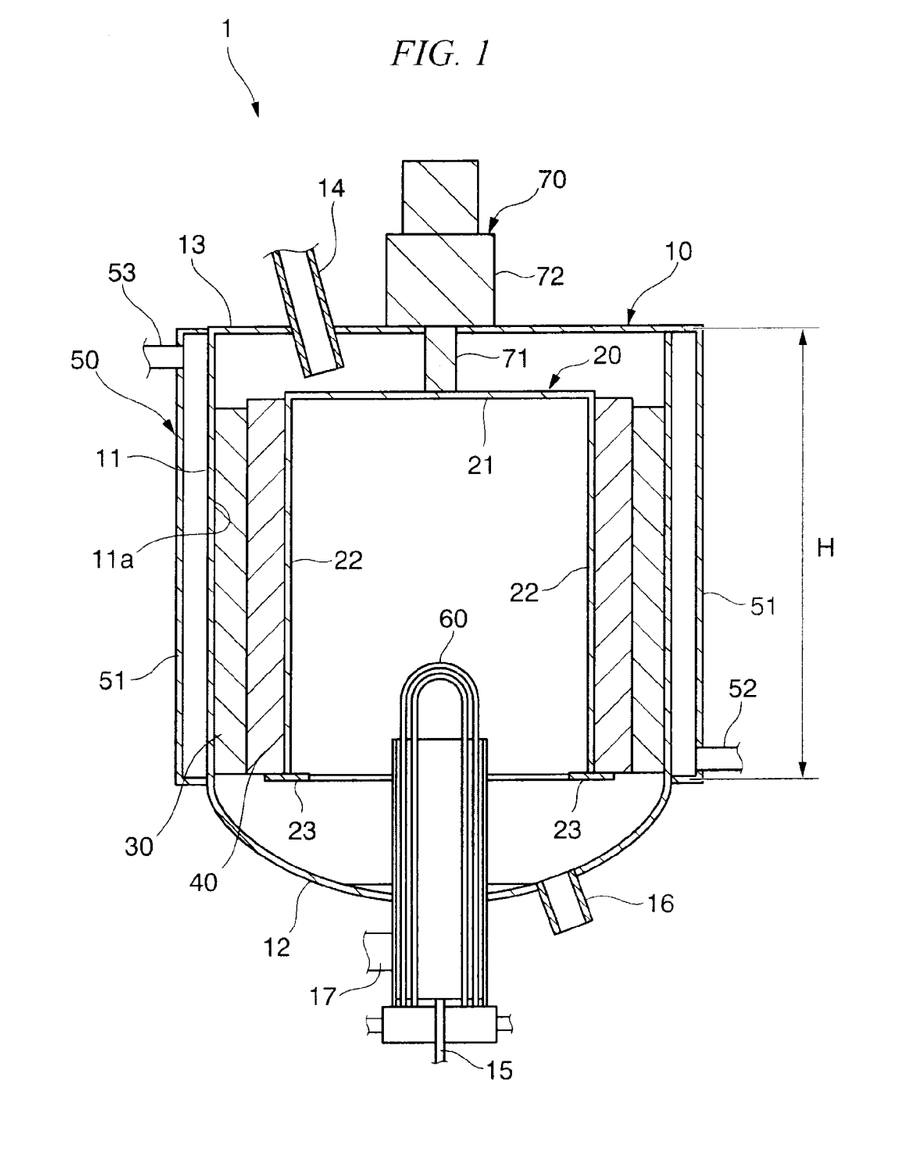
FIG. 1 is a longitudinal sectional view illustrating an embodiment of a vertical centrifugal thin film evaporator of the present invention.

The vertical centrifugal thin film evaporator of the embodiment is illustrated in FIG. 1. The vertical centrifugal thin film evaporator 1 of the embodiment purifies a material to be purified (or a purifying target material) contained in a liquid to be processed (or a processing target material), and is equipped with an evaporation container 10, a rotor 20, a wiper 30, a fixing support 40, a heater 50, a condenser 60, and a drive means 70.

The evaporation container 10 is equipped with a cylindrical body 11 in which an central axis of a circle is set in a vertical direction, a funnel-shaped container bottom 12 that is located at a lower side relative to the cylindrical body 11 and is reduced in diameter as it goes downward, a lid 13 that seals an upper side of the cylindrical body 11, a liquid lead-in pipe 14 that introduces the processing target liquid into an interior of the cylindrical body 11, and a bottom discharge pipe 16 that is mounted on the container bottom 12.

An outer diameter of the cylindrical body 11 is not particularly limited, and is set to, for instance, 0.1 to 2.0 m. A height of the cylindrical body 11 is not particularly limited as well, and is set to, for instance, 0.4 to 6.0 m.

As a material of the cylindrical body 11, a material that is rarely deformed by heating is favorably used. For example, carbon steel, stainless steel, or glass lining may be used. The container bottom 12 and the lid 13 may be formed of the same material as the cylindrical body 11.

The liquid lead-in pipe 14 passes through the lid 13, and is disposed to allow the processing target liquid to be introduced toward a disk part 21 of the rotor 20 to be described below.

The rotor 20 rotates the interior of the cylindrical body 11. In the embodiment, the rotor 20 is equipped with a disk part 21 that is horizontally installed in the interior of the cylindrical body 11, a fixing support mounting part 22 on which the fixing support 40 is mounted, and a ring part 23 that is mounted on a lower end of the fixing support mounting part 22 and is formed along an inner circumferential surface of the cylindrical body 11.

The fixing support mounting part 22 is provided for a periphery of a lower surface of the disk part 21 in a vertical direction. Further, the fixing support mounting part 22 is made up of numerous parts, which are mounted at regular intervals in a circumferential direction of the disk part 21.

A material of the rotor 20 is not particularly limited. For example, carbon steel, stainless steel, or glass lining may be used.

The drive means 70 is connected to the center of an upper surface of the disk part 21 in the rotor 20. The rotor 20 is rotated by driving of the drive means 70, and the fixing support mounting part 22 is adapted to rotate along the inner circumferential surface 11a of the cylindrical body 11. Further, the rotation of the fixing support mounting part 22 is adapted to cause the fixing support 40 mounted on the fixing support mounting part 22 to be rotated along the inner circumferential surface 11a of the cylindrical body 11.

The wiper 30 slides on the inner circumferential surface of cylindrical body 11, forming a liquid film of the processing target liquid on the inner circumferential surface of the cylindrical body 11. The wiper rotating together with the rotating rotor may also be called a rotor blade.

Figure 2:
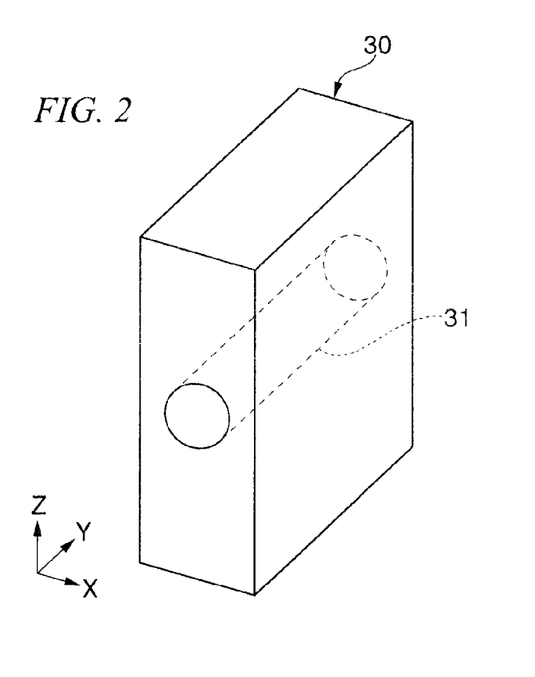
FIG. 2 is a perspective view illustrating an example of a wiper constituting the vertical centrifugal thin film evaporator of FIG. 1.
Figure 3:
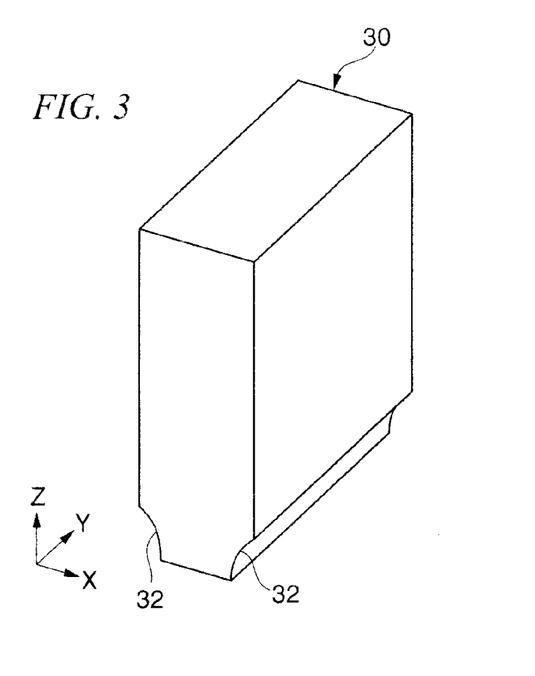
FIG. 3 is a perspective view illustrating another example of the wiper constituting the vertical centrifugal thin film evaporator of FIG. 1.

A shape of the wiper 30 is not particularly limited. Typically, an approximately rectangular parallelepiped as illustrated in FIGS. 2 and 3 is used. The wiper 30 of the approximately rectangular parallelepiped may be configured such that one wiper is used as one unit, or numerous wipers may be used as one unit by serial arrangement in a vertical direction. Numerous units may be used as one set by serial arrangement in a vertical direction. A length of one wiper having the shape of the approximately rectangular parallelepiped is preferably 1 to 80% with respect to a height H of the cylindrical body 11, more preferably 3 to 50%, and even more preferably 5 to 30%. Here, a lowest point of the height H is set to a tangent line of an end plate that becomes the bottom of the cylindrical body 11. If the length of the wiper 30 is not more than the upper limit, the wiper has an adequate length, and is made inexpensive in conjunction with easy maintenance. If the length of the wiper 30 is not less than the lower limit, the number of units can be reduced, and in the case of forming a through-hole as will be described below, sufficient strength can be secured.

A length of one set of wipers is preferably 60 to 99% with respect to the height H of the cylindrical body 11, more preferably 70 to 98%, and even more preferably 80 to 95%. When the length of one set of wipers is not less than 60% with respect to the height H, the processing target liquid can be evaporated with high efficiency. When the length of one set of wipers is not more than 99% with respect to the height H, the maintenance is made easy.

The wiper 30 preferably has a length of 0.005 to 0.1 m in a widthwise direction thereof (an X direction in FIGS. 2 and 3, or a horizontal direction of a face coming into contact with the cylindrical body 11). The wiper 30 preferably has a thickness of 0.02 to 0.05 m.

Further, a face of the wiper 30 which is in contact with the inner circumferential surface of the cylindrical body 11 may be provided with a slanted groove inclined such that, the rear in a rotational direction is lowered at the time of rotation. If the slanted groove is formed in the wiper 30, it is possible to improve purification performance of the purifying target material.

A material of the wiper 30 is not particularly limited as long as it does not damage the cylindrical body 11. For example, polytetrafluoroethylene, carbon, polyethylene, polypropylene, or a combination thereof may be used.

The fixing support 40 is adapted to be able to hold the wiper 30, and fixes the wiper 30 to the rotor 20.

Figure 4:
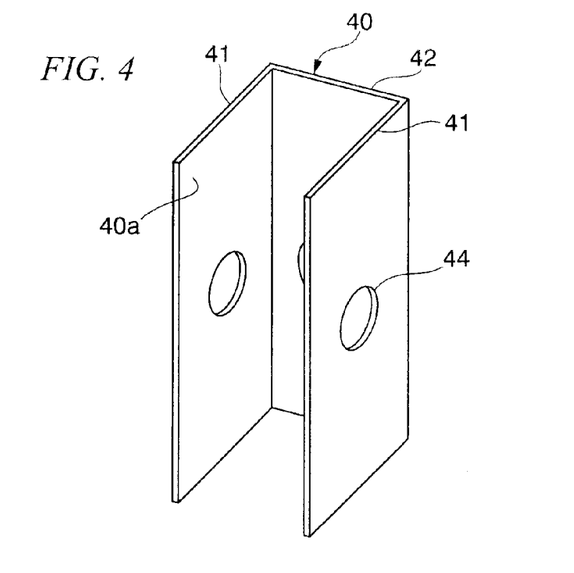
FIG. 4 is a perspective view illustrating an example of a fixing support constituting the vertical centrifugal thin film evaporator of FIG. 1.
Figure 5:
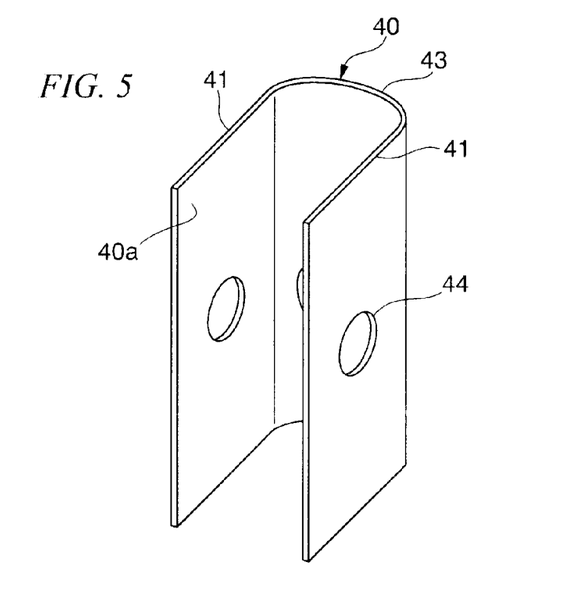
FIG. 5 is a perspective view illustrating another example of the fixing support constituting the vertical centrifugal thin film evaporator of FIG. 1.
Figure 6:
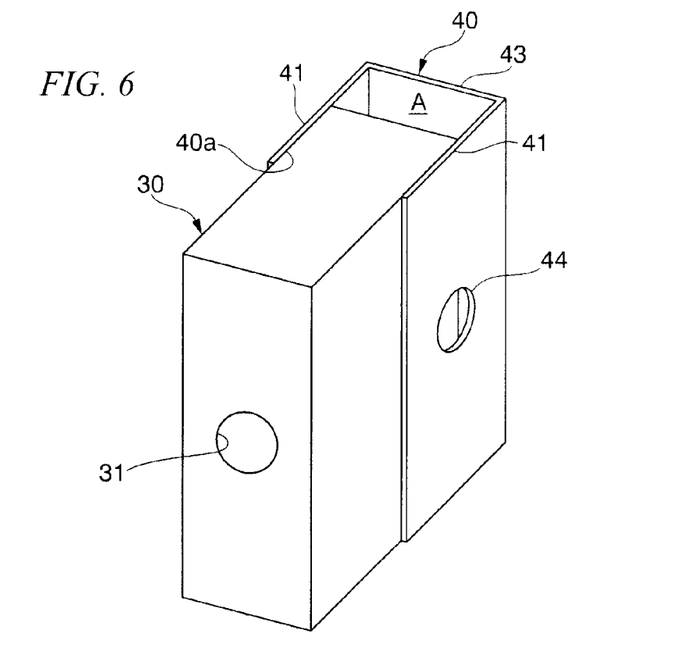
FIG. 6 is a perspective view illustrating a situation in which the wiper illustrated in FIG. 2 is held by the fixing support illustrated in FIG. 4.

The fixing support 40 may include, for instance, one made up of two tabular parts 41 and 41 parallel to each other and a flat-plate-shaped connecting part 42 connecting the tabular parts 41 and 41 as illustrated in FIG. 4, and one (whose horizontal cross section is in a U shape) made up of two tabular parts 41 and 41 parallel to each other and a curved-plate-shaped connecting part 43 connecting the tabular parts 41 and 41 as illustrated in FIG. 5. In these fixing supports 40, a furrowed part 40a is defined by the tabular parts 41 and the connecting part 42 or 43, and as illustrated in FIG. 6, the wiper 30 is adapted to be fitted into the furrowed part 40a so as to be able to be held in the furrowed part 40a.

The fixing support 40 is mounted on the fixing support mounting part 22 of the rotor 20, and is thus disposed in a vertical direction. For this reason, the furrowed part 40a is also formed in a vertical direction.

The furrowed part 40a is formed in slightly greater dimensions than those of the wiper 30 so as to be able to house the wiper 30. Further, the furrowed part 40a is preferably dimensioned to movably fix the wiper 30 in order to cause the wiper 30 to be pressed against the inner circumferential surface 11a of the cylindrical body 11 by a centrifugal force during the rotation.

The number of fixing supports 40 is not particularly limited, but it is preferably 2 to 20. Further, an even number of fixing supports 40 is preferably disposed in symmetry with respect to the central axis of the rotor 20.

A material of the fixing support 40 preferably includes stainless steel or glass lining.

At least one of the wiper 30 and the fixing support 40 is provided with a liquid-withdrawing structure that communicates between a space A (see FIG. 6) surrounded by the wiper 30 and the fixing support 40 and a space outside the wiper 30 and the fixing support 40.

The liquid-withdrawing structure may include a through-hole 31 formed in the wiper 30 (see FIG. 2), notches 32 formed in the wiper 30 (see FIG. 3), and through-holes 44 formed in the fixing support 40 (see FIGS. 4 and 5), any one of which may be adopted, or two or more of which may be combined.

The through-hole formed in the wiper 30 is particularly the through-hole 31 formed in a thickness direction (a Y direction in FIGS. 2 and 3, i.e. a direction that is perpendicular to the X direction and is horizontal) of the wiper 30. The through-hole 31 may be present at any one or two or more of an upper portion (a portion located ⅓ of the full length of the wiper at an upper side), a lower portion (a portion located ⅓ of the full length of the wiper at a lower side), and an intermediate portion (a portion between the upper portion and the lower portion) of the wiper 30. The number of through-holes 31 formed in each portion may be one or two or more.

A lower end of the fixing support 40 may be provided with a bottom plate for preventing the wiper 30 from falling. However, in this case, the processing target liquid is easily retained at a lower portion of the space A surrounded by the wiper 30 and the fixing support 40, and thus at least one through-hole 31 is preferably formed in the lower portion of the wiper 30.

A cross-sectional shape of the through-hole 31 of the wiper 30 may include a quadrangular shape, a triangular shape, a circular shape, a semicircular shape, and an oval shape. The through-hole 31 preferably has an opening area of 1 to 500 mm$^2$ (when the cross-sectional shape thereof is the circular shape, an opening diameter of 1 to 15 mm). If the opening area of the through-hole 31 is not more than the upper limit, the wiper 30 has sufficient strength. If the opening area of the through-hole 31 is not less than the lower limit, it is possible to further prevent the retention of the processing target liquid.

Each notch 32 of the wiper 30 is particularly a notch formed in an edge of the wiper 30 in the thickness direction (the Y direction). As such a notch 32 is formed, a gap is formed between the wiper 30 and the fixing support 40, and the processing target liquid can pass through the wiper in the thickness direction (the Y direction) of the wiper 30.

As the notches 32 are formed, a gap generated when the wiper 30 is mounted on the fixing support 40 preferably has an opening area of 1 to 500 mm$^2$. If the opening area of the gap is not more than the upper limit, the wiper 30 has sufficient strength. If the opening area of the gap is not less than the lower limit, it is possible to further prevent the retention of the processing target liquid.

Each through-hole 44 formed in the fixing support 40 may be present at any one or two or more of an upper portion (a portion located ⅓ of the full length of the wiper at an upper side), a lower portion (a portion located ⅓ of the full length of the wiper at a lower side), and an intermediate portion (a portion between the upper portion and the lower portion) of the fixing support 40. The number of through-holes 44 formed in each portion may be one or two or more.

In terms of the fact that the retention of the processing target liquid can be further prevented, at least one through-hole 44 is preferably formed in the lower portion of the fixing support 40.

A cross-sectional shape of the through-hole 44 of the fixing support 40 may include a quadrangular shape, a triangular shape, a circular shape, a semicircular shape, and an oval shape. The through-hole 44 preferably has an opening area of 1 to 500 mm$^2$ (when the cross-sectional shape thereof is the circular shape, an opening diameter of 1 to 15 mm). If the opening area of the through-hole 44 is not more than the upper limit, the fixing support 40 has sufficient strength. If the opening area of the through-hole 44 is not less than the lower limit, it is possible to further prevent the retention of the processing target liquid.

The heater 50 according to the embodiment is equipped with a jacket 51 provided outside the cylindrical body 11, and heating medium lead-in/out pipes 52 and 53 for leading a heating medium into or out of the jacket 51. As the heating medium, steam or heated oil is used.

In the heater 50, the heating medium is led into the jacket 51 through one of the heating medium lead-in/out pipes 52 and 53, and is then led out through the other of the heating medium lead-in/out pipes 52 and 53, thereby allowing the cylindrical body 11 adjacent to the jacket 51 to be heated. This allows the inner circumferential surface of the cylindrical body 11 to be heated. If the heating medium is the steam, the steam is preferably introduced from the heating medium lead-in/out pipe 53, and is discharged from the heating medium lead-in/out pipe 52.

The condenser 60 is configured such that a cooling medium flows in an interior thereof, and cools and condenses a vapor of a material evaporating from the inner circumferential surface of the cylindrical body 11. The condenser 60 is provided with a distillate discharge pipe 15 that discharges a distillate obtained by condensation, and a vacuum suction pipe 17 for connecting a vacuum suction means (not illustrated) to the condenser 60. The installation of the condenser 60 reduces a pressure loss between an evaporation plane and a condensation plane, and enables high-vacuum operation.

The condenser 60 according to the embodiment is inserted from the side of the container bottom 12 into the interior of the evaporation container 10. A surface area of the condenser 60 in the interior of the evaporation container 10 is preferably 0.1 to 50 m$^2$.

A temperature of the cooling medium is properly determined by properties of materials contained in the processing target liquid, an operating pressure, and so on, but it is in a range of, for instance, −10 to 50° C.

The drive means 70 is equipped with a shaft 71 connected to the center of the upper surface of the disk part 21, and a motor 72 rotating the shaft 71.

The drive means 70 is adapted to drive the motor 72 to rotate the shaft 71, thereby rotating the rotor 20. The rotation of the rotor 20 is adapted to cause the wiper 30 to slide on the inner circumferential surface 11a of the cylindrical body 11.

In purifying the purifying target materials using the vertical centrifugal thin film evaporator 1, the cylindrical body 11 is heated by the heater 50, and the interior of the evaporation container 10 is cooled by the condenser 60. Further, the drive means 70 rotates the rotor 20, and the resultant centrifugal force presses the wiper 30 against the inner circumferential surface 11a of the cylindrical body 11. Thereby, the wiper 30 is caused to slide on the inner circumferential surface 11a of the cylindrical body 11.

In this state, the processing target liquid containing the unpurified materials is introduced onto the disk part 21 inside the evaporation container 10 using the liquid lead-in pipe 14. The processing target liquid introduced to the disk part 21 is scattered and attached to the inner circumferential surface 11a of the cylindrical body 11 by a centrifugal force caused by the rotation of the disk part 21, and what is more, flows down the inner circumferential surface 11a of the cylindrical body 11. Here, the processing target liquid flowing down the inner circumferential surface 11a is stretched by the wiper 30 sliding on the inner circumferential surface of the cylindrical body 11, and thus a liquid film is formed.

Since the inner circumferential surface 11a of the cylindrical body 11 is heated by the heater 50, a material having a low boiling point and a material having a medium boiling point, which are contained in the liquid film formed on the inner circumferential surface 11a, are evaporated, and a material having a high boiling point flows down the inner circumferential surface 11a with no change. Since the interior of the evaporation container 10 is cooled by the condenser 60, the evaporated materials are lowered in temperature. The material having a medium boiling point condensed by a fall in temperature is discharged from the evaporation container 10 via the distillate discharge pipe 15. The material having a low boiling point that is not condensed despite a fall in temperature is discharged from the vacuum suction pipe 17. In contrast, the material having a high boiling point is discharged from the evaporation container 10 via the bottom discharge pipe 16.

In the aforementioned vertical centrifugal thin film evaporator 1, the liquid-withdrawing structure is formed on at least one of the wiper 30 and the fixing support 40, and the processing target liquid can be prevented from being retained in the space A (see FIG. 6) between the wiper 30 and the fixing support 40. For this reason, in the case of containing a material that is easily polymerized and solidified by heat, the processing target liquid can inhibit from being polymerized and solidified, and stabilize the operation of the vertical centrifugal thin film evaporator 1. In the case of containing a material that is apt to thermal degradation, the processing target liquid can suppress the thermal degradation, and reduce an influence on the purification. Further, the vertical centrifugal thin film evaporator 1 is also suitable for purification of high-viscosity materials.

The vertical centrifugal thin film evaporator 1 is particularly favorable to purification of a monomer that is easily polymerized and solidified by heat and has a vinyl group (hereinafter referred to as a "vinyl monomer").

<Monomer Purification Method>

An embodiment of a vinyl monomer purification method using the vertical centrifugal thin film evaporator will be described. In this embodiment, the material having a medium boiling point among the components contained in the processing target liquid is a vinyl monomer.

First, the cylindrical body 11 is heated by the heater 50, the interior of the cylindrical body 11 is cooled by the condenser 60, and the rotor 20 is rotated to cause the wiper 30 to slide on the inner circumferential surface 11a of the cylindrical body 11. In this state, the processing target liquid containing the vinyl monomer is introduced to the disk part 21 inside the cylindrical body 11 by the liquid lead-in pipe 14. The processing target liquid introduced to the disk part 21 is attached to the inner circumferential surface 11a of the cylindrical body 11 by the rotation of the disk part 21, and also flows down the inner circumferential surface 11a of the cylindrical body 11. At this time, the wiper 30 slides on the inner circumferential surface of the cylindrical body 11, and thereby a liquid film is formed.

Since the inner circumferential surface 11a of the cylindrical body 11 is heated by the heater 50, the liquid film, particularly, a material having a low boiling point and a vinyl monomer having a medium boiling point are evaporated. The vinyl monomer evaporated inside the cylindrical body 11 is lowered in temperature by the condenser 60, is condensed, and is discharged from the evaporation container 10 via the distillate discharge pipe 15. The material having a low boiling point that is not condensed is discharged from the vacuum suction pipe 17. Further, the residual liquid that flows down the inner circumferential surface 11a and comes up to the container bottom 12 is discharged from the container bottom 12 via the bottom discharge pipe 16. The discharged residual liquid may be mixed with the processing target liquid introduced to the evaporation container 10. Since the vinyl monomer is also contained in the residual liquid at a small amount, if the residual liquid is mixed with the processing target liquid, it is possible to improve a yield.

In the purification method, a speed of rotation of the rotor 20 may be properly determined such that a pressure under which the wiper 30 is pressed against the inner circumferential surface 11a becomes an adequate pressure, but it is preferably set to 10 to 200 rpm.

A temperature of the inner circumferential surface 11a of the cylindrical body 11 is properly determined by properties of the vinyl monomer to be purified and components other than the monomer, and an operating pressure, but it is preferably set to 50 to 120° C. A component having a high boiling point can be discharged from the bottom discharge pipe 16 under adequate heating conditions.

An internal pressure of the evaporation container 10 may be any of an applied pressure, an ordinary pressure, and a reduced pressure, but in order to further inhibit the vinyl monomer from being polymerized and solidified, the internal pressure is preferably reduced to maintain a low temperature. In the case of reducing a pressure, the corresponding pressure is preferably set to 0.01 to 80 kPa (absolute pressure).

The vinyl monomer to which the purification method is applied may include, for instance, an acrylic monomer, a styrene monomer, and a vinyl acetate monomer, but the acrylic monomer is favorable because the effects of the present invention are significantly exerted.

The acrylic monomer may include a (meth)acrylic acid; alkyl(meth)acrylate such as methyl(meth)acrylate, ethyl (meth)acrylate, n-butyl(meth)acrylate, isobutyl(meth)acrylate, tert-butyl(meth)acrylate, stearyl(meth)acrylate, 2-ethyl hexyl(meth)acrylate, or lauryl(meth)acrylate; cyclohexyl (meth)acrylate; phenyl(meth)acrylate; benzyl(meth)acrylate; isobornyl(meth)acrylate, glycidyl(meth)acrylate; tetrahydrofurfuryl(meth)acrylate; allyl(meth)acrylate, trifluoroethyl(meth)acrylate; dialkylaminoethyl(meth)acrylate such as dimethylaminoethyl(meth)acrylate, dimethylaminoethylmethyl chloride salt(meth)acrylate, dimethylaminoethylbenzyl chloride salt(meth)acrylate, or diethyl aminoethyl(meth)acrylate; di and tri(meth)acrylate such as ethylene glycol di(meth)acrylate, triethylene glycol di(meth) acrylate, 1,3-butylene glycol di(meth)acrylate, 1,6-hexanediol di(meth)acrylate, polybutylene glycol di(meth)acrylate, or trimethylol propane tri(meth)acrylate; and hydroxyalkyl (meth)acrylate such as 2-hydroxyethyl(meth)acrylate, 2-hydroxypropyl(meth)acrylate, 2-methoxyethyl(meth)acrylate, or 2-ethoxyethyl(meth)acrylate.

In the monomer production method, since the vertical centrifugal thin film evaporator 1 in which the liquid-withdrawing structure is formed on at least one of the wiper 30 and the fixing support 40 is used, it is possible to prevent the processing target liquid from being retained between the wiper 30 and the fixing support 40, and to inhibit the vinyl monomer from being polymerized and solidified. For this reason, it is possible to stably operate the vertical centrifugal thin film evaporator.

The present invention is not limited to the aforementioned embodiments.

In the evaporation container, the liquid lead-in pipe may be connected to the cylindrical body so that the processing target liquid can be introduced to the inner circumferential surface of the cylindrical body.

In the rotor, instead of mounting the fixing support mounting part on the disk part, the fixing support mounting part may be mounted on the rotary shaft connected to the shaft of the drive means.

EXAMPLES

Example 1

2-hydroxyethyl methacrylate contained in a processing target liquid was purified using an evaporator which is the vertical centrifugal thin film evaporator illustrated in FIG. 1 and has a height of 3350 mm and whose cylindrical body has a height of 1920 mm.

As the processing target liquid, a liquid containing 95.5% by mass of 2-hydroxyethyl methacrylate, 4.1% by mass of impurities having a high boiling point (diesters or dialkylene glycol monoesters), and 0.4% by mass of impurities having a low boiling point (ethylene glycol) was used.

As the wiper 30, a wiper which was a rectangular parallelepiped having a height of 175 mm, a width of 15 mm, and a thickness of 30 mm and in which, as illustrated in FIG. 3, each notch 32 (liquid-withdrawing structure) was formed in a thickness direction (Y direction) up to a height of 50 mm from a lower end in a height direction (Z direction) such that a width of the lower end is 5 mm, and a wiper which was a rectangular parallelepiped having a height of 175 mm, a width of 15 mm, and a thickness of 30 mm and in which no notch (liquid-withdrawing structure) was formed were used. To be specific, a wiper in which the notches were formed was used as a lowermost wiper, and four wipers in which no notches were formed were stacked on the lowermost wiper in series, thereby becoming one unit. These two units were vertically provided to be a set of wipers, and a total of four sets of wipers were provided at positions between which a difference of 90 degrees was present when the shaft 71 was viewed from the top.

As the fixing support 40, four fixing supports, each of which was made up of the two tabular parts 41 and one connecting part 42 and had the furrowed part for holding the wiper, and the through-holes (liquid-withdrawing structures) were not formed thereof as illustrated in FIG. 4, were used to fix the four sets of wipers.

As the cylindrical body 11, one having an inner diameter of 600 mm was used, and a temperature of the inner circumferential surface 11a was set to about 120° C. by the heater 50. A pressure inside the evaporation container 10 was set to 0.13 kPa (absolute pressure).

A speed of rotation of the rotor 20 was set to 160 rpm.

Figure 7:
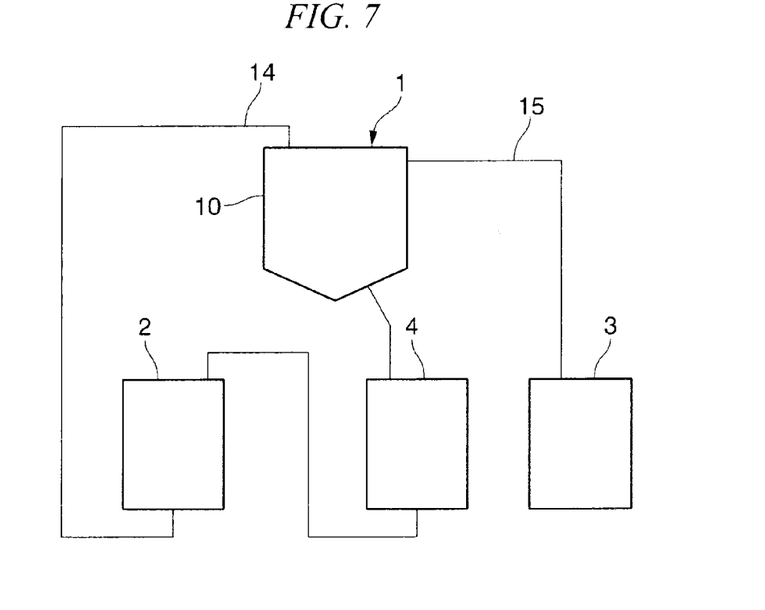
FIG. 7 is a schematic view illustrating a monomer purification apparatus used in the embodiments.

In the purification, 5820 kg of processing target liquid was put into a supply tank 2 as illustrated in FIG. 7, was introduced from the supply tank 2 into the interior of the evaporation container 10 via the liquid lead-in pipe 14 at 1600 kg/hour, and 2-hydroxyethyl methacrylate was evaporated and concentrated in the evaporation container 10. Thereby, a distillate containing 2-hydroxyethyl methacrylate was discharged from the distillate discharge pipe 15, and was sent to a recovery tank 3. Here, a distillation speed of the distillate was 800 to 900 kg/h.

Further, after the container discharge liquid was discharged from the bottom discharge pipe 16, and was temporarily stored in the container discharge liquid tank 4, the container discharge liquid was adapted to be sent back to the supply tank 2, and to be sent to the vertical centrifugal thin film evaporator 1 again.

Thus, the purification was conducted until the distillate in the recovery tank 3 reached 5000 kg, and 2-hydroxyethyl methacrylate having the purity of 97.5% by mass was recovered.

Further, while the purification was continued for one month, the operation was conducted stably without causing problems such as polymerization of 2-hydroxyethyl methacrylate and a rise in agitation electric power.

Comparative Example 1

2-hydroxyethyl methacrylate was purified according to the same method as in Example 1, except that the through-holes or the notches were not formed in all of the wipers. As a result, a polymer was produced between the wiper and the fixing support, so that the operation was forced to make a stop for two weeks.

Example 2

2-hydroxyethyl methacrylate was purified according to the same method as in Example 1, exclusive of using the fixing support, in the rear and both sides of which the through-hole having a diameter of 3 mm was formed at intervals of 150 mm.

While the purification was continued for one month, the operation was conducted stably without causing problems such as polymerization of 2-hydroxyethyl methacrylate and a rise in agitation electric power.

EXPLANATIONS OF LETTERS OR NUMERALS

1: vertical centrifugal thin film evaporator
10: evaporation container
11: cylindrical body
12: container bottom
13: lid
14: liquid lead-in pipe
15: distillate discharge pipe
16: bottom discharge pipe
17: vacuum suction pipe
20: rotor
21: disk part
22: fixing support mounting part
23: ring part
30: wiper
31: through-hole
32: notch
40: fixing support
40a: furrowed part
41: tabular part
42, 43: connecting part
44: through-hole
50: heater 51: jacket
52, 53: heating medium lead-in/out pipe
60: condenser
70: drive means
71: shaft
72: motor

The invention claimed is:

1. A vertical centrifugal thin film evaporator comprising:
a cylindrical body in which a central axis of a circle is set in a vertical direction,
a rotor configured to rotate an interior of the cylindrical body in a circumferential direction thereof,
a wiper configured to slide on an inner circumferential surface of the cylindrical body,
a fixing support configured to fix the wiper and mounted on the rotor, and
a heater configured to heat a circumferential surface of the cylindrical body,
wherein at least one wiper and the fixing support has a liquid-withdrawing structure in the radial direction of the rotor (Y direction) that communicates between a space surrounded by the wiper and the fixing support and a space outside the wiper and the fixing support, and
the X direction indicates a tangential direction to the rotor, the Y direction indicates a radial direction of the rotor, and the Z direction indicates a vertical direction.

2. The vertical centrifugal thin film evaporator according to claim 1, wherein the wiper has a through-hole formed as the liquid-withdrawing structure.

3. The vertical centrifugal thin film evaporator according to claim 1, wherein the wiper has a notch formed as the liquid-withdrawing structure.

4. The vertical centrifugal thin film evaporator according to claim 1, wherein the fixing support has a through-hole formed as the liquid-withdrawing structure.

5. A monomer purification method, said method comprising
purifying a liquid with the vertical centrifugal thin film evaporator of claim 1, wherein said liquid comprises a monomer having a vinyl group.

6. The vertical centrifugal thin film evaporator according to claim 2, wherein the wiper has a notch formed as the liquid-withdrawing structure.

7. The vertical centrifugal thin film evaporator according to claim 2, wherein the fixing support has a through-hole formed as the liquid-withdrawing structure.

8. The vertical centrifugal thin film evaporator according to claim 3, wherein the fixing support has a through-hole formed as the liquid-withdrawing structure.

9. The method according to claim 5, wherein the monomer having the vinyl group is one or more of (meth)acrylic acid; alkyl (meth)acrylate such as methyl (meth)acrylate, ethyl (meth)acrylate, n-butyl (meth)acrylate, isobutyl (meth)acrylate, tert-butyl (meth)acrylate, stearyl (meth)acrylate, 2-ethyl hexyl (meth)acrylate, or lauryl (meth)acrylate; cyclohexyl (meth)acrylate; phenyl (meth)acrylate; benzyl (meth)acrylate; isobornyl (meth)acrylate; glycidyl (meth)acrylate; tetrahydrofurfuryl (meth)acrylate; allyl (meth)acrylate, trifluoroethyl (meth)acrylate; dialkylaminoethyl (meth)acrylate such as dimethylaminoethyl (meth)acrylate, dimethylaminoethylmethyl chloride salt (meth)acrylate, dimethylaminoethylbenzyl chloride salt (meth)acrylate, or diethylaminoethyl (meth)acrylate; di and tri(meth)acrylate such as ethylene glycol di(meth)acrylate, triethylene glycol di(meth)acrylate, 1,3-butylene glycol di(meth)acrylate, 1,6-hexanediol di(meth)acrylate, polybutylene glycol di(meth)acrylate, or trimethylol propane tri(meth)acrylate; and hydroxyalkyl (meth)acrylate such as 2-hydroxyethyl (meth)acrylate, 2-hydroxypropyl (meth)acrylate, 2-methoxyethyl (meth)acrylate, and 2-ethoxyethyl (meth)acrylate.

10. The method according to claim 5, wherein the purification is done at a pressure of from 0.01 to 80 kPa.

11. The method according to claim 5, wherein a temperature setting of the inner circumferential surface is from 50 to 120° C. and a speed of rotation is from 10 to 200 rpm.

12. The vertical centrifugal thin film evaporator according to claim 1, wherein the wiper, the fixing support, or both have a through hole formed in the radial direction of the rotor (Y direction).

* * * * *